United States Patent [19]

Kunii et al.

[11] Patent Number: 5,228,911
[45] Date of Patent: Jul. 20, 1993

[54] OXIDIZED GRAPHITE FLAKY PARTICLES AND PIGMENTS BASED THEREON

[75] Inventors: Koshiro Kunii; Katsuhisa Nitta; Kunimitsu Ohira, all of Iwaki, Japan

[73] Assignee: Merck Patent Gesellschaft mit beschrankter Haftung, Darmstadt, Fed. Rep. of Germany

[21] Appl. No.: 869,459

[22] Filed: Apr. 17, 1992

[30] Foreign Application Priority Data

Apr. 18, 1991 [JP] Japan ................................ 91-177834
May 24, 1991 [JP] Japan ................................ 91-221316

[51] Int. Cl.⁵ ................................................ C09C 1/44
[52] U.S. Cl. .................................... 106/478; 106/472; 106/474
[58] Field of Search ............... 106/472, 474, 478, 436

[56] References Cited

U.S. PATENT DOCUMENTS

| | | | |
|---|---|---|---|
| 3,481,754 | 12/1968 | Lewis et al. | 106/478 |
| 3,992,218 | 11/1976 | Suetsuhu et al. | 106/478 |
| 4,435,377 | 3/1984 | Rothbühr | 423/460 |
| 5,074,917 | 12/1991 | Persello | 106/436 |

FOREIGN PATENT DOCUMENTS 911270 10/1972 Canada .
16531 2/1974 Japan .
87422 7/1977 Japan .

OTHER PUBLICATIONS

Abstract of JP 87,422, dated 1977.
Abstract of JP 16,531, dated 1974.
Letter from T. Itoh, of E. Merck discussing Japanese patents JP 16,531 and JP 87,422.

*Primary Examiner*—Mark L. Bell
*Assistant Examiner*—Chris Gallo
*Attorney, Agent, or Firm*—Millen, White, Zelano & Branigan

[57] ABSTRACT

The invention relates to oxidized graphite flaky particles obtainable
- by oxidizing graphite flaky particles in an oxygen-containing atmosphere at 200°–500° C.,
- by suspending graphite flaky particles in aqueous medium and oxidizing them with a water-soluble oxidizing agent or
- by oxidizing graphite flaky particles in an oxygen-containing atmosphere, suspending these oxidized particles in an aqueous medium and oxidizing them further with a water-soluble oxidizing agent, and to pigments based thereon.

14 Claims, No Drawings

OXIDIZED GRAPHITE FLAKY PARTICLES AND PIGMENTS BASED THEREON

FIELD OF THE INVENTION

The present invention relates to oxidized graphite flaky particles and pigments based thereon which are characterized by a high light and weather resistance and by a good chromaticity. The invention furthermore relates to a process for producing the oxidized graphite flaky particles and the pigments based thereon.

BACKGROUND OF THE INVENTION

Among those pigments formed by coating a flaky substrate with a metal oxide having a high refractive index are titanium oxide-coated mica pigment and iron oxide-coated mica pigment. These pigments are characterized by the optical interference they produce. For the interference color to have a high saturation, it is necessary that the surface of flaky substrate particles be coated with a uniform, dense layer of fine, uniform particles of metal oxide. This metal oxide layer produces an interference color when its optical thickness is properly controlled.

Pigments producing an interference color are attracting attention because of their aesthetic nature, and they are now in general use for paint, plastics, ink, and cosmetics. However, a metal oxide-coated mica pigment is limited in its application due to its poor hiding power inherent in its optical characteristics. This poor hiding power leads to dichroism which has an adverse effect on the color. (Dichroism is due to interference of light reflected at a certain angle by a white substrate and a paint of poor hiding power applied thereon.)

Coloring pigments are required to have a high hiding power and superior chromaticity as well as good light resistance and weather resistance if they are to be added to automotive finishing paints, architectural paints, printing inks, and plastic products for outdoor use. In the case of automotive finishing paints, the requirements are met by graphite flaky particles coated with a metal oxide. Graphite flaky particles have a high hiding power and adsorb transmitting interference colors owing to their black smooth surface, and the metal oxide coating produces interference colors.

Titanium dioxide-coated graphite pigments are known as disclosed in Japanese Patent Publication No. 3824/1974 and Japanese Patent Laid open No. 87422/1977. They do not necessarily meet requirements for various color effects. According to the first disclosure, the pigment is prepared by suspending an untreated graphite substrate in water with stirring and then coating it with titanium dioxide. A disadvantage of this process is that the graphite substrate is not thoroughly dispersed in water and hence is not uniformly coated with titanium dioxide. The resulting pigment, therefore, does not produce a satisfactory interference color. According to the second disclosure, the pigment is prepared by suspending natural flaky graphite (as the substrate) in a titanyl sulfate solution and hydrolyzing it with heating, thereby coating the substrate with titanium dioxide. A disadvantage of this process is that the titanium dioxide coating is not so dense as required and involves difficulties in controlling its thickness and particle size.

The pigments disclosed in Japanese Patent Publication Nos. 3824/1974 and 16531/1974 and Japanese Patent Laid-open No. 87422/1974. Thus do not necessarily produce good interference colors, nor do they exhibit satisfactory light resistance and weather resistance.

SUMMARY OF THE INVENTION

It is an object of the present invention to provide a flaky graphite-type substrate with improved properties and pigments being based thereon said graphite flake pigment exhibiting good or even outstanding light resistance, weather resistance and or chromaticity in comparison to prior art pigments.

It is another object of the present invention to provide a process for producing such pigments under controllable conditions.

With conventional technology for titanium dioxide-coated graphite pigments, it was impossible to make a dense and uniform coating and hence it was impossible to produce interference colors of high saturation and to control their chromaticity. Moreover, conventional titanium dioxide-coated graphite pigments present a problem associated with anatase titanium dioxide used for coating. They do not exhibit satisfactory light resistance and weather resistance (and hence they discolor with time) when used for paints, inks, and plastics.

The invention will be described in more detail in the following.

The present invention is embodied in one aspect by oxidized graphite flaky particles obtainable
- by oxidizing graphite flaky particles in an oxygen-containing atmosphere at 200°–500° C.,
- by suspending graphite flaky particles in an aqueous medium and oxidizing them with a water-soluble oxidizing agent or a combination of these steps, preferably,
- by oxidizing graphite flaky particles in an oxygen-containing atmosphere, suspending these oxidized particles in an aqueous medium and oxidizing them further with a water-soluble oxidizing agent.

The employed graphite flaky particles preferably have a diameter of 0.5–150 μm, more preferably 1–60 μm, and a thickness preferably of 0.05–10 μm, more preferably 0.1–3 μm.

The surface oxidation of graphite flaky particles can be accomplished by heating in an oxygen-containing atmosphere at, e.g., 200°–500° C. for 0.15–15 hours, preferably 0.25–3 hours. This heat treatment increases the number of carboxyl groups and phenolic hydroxyl groups on the surface of graphite flaky particles. However, excessive heat treatment at a higher temperature and for a longer time than specified above gives rise to surface irregularities and pores on the surface of graphite flaky particles, which embrittle them and make them less preferable for use as a substrate for metal oxide coating.

Another process employs a water-soluble oxidizing agent for the oxidation treatment. It includes, for example, hydrogen peroxide, sodium peroxide, sodium perchlorate, potassium permanganate, potassium manganate, potassium chromate, sodium chromate, potassium bichromate, sodium bichromate, formic acid, acetic acid, nitric acid, potassium nitrate, sodium nitrate, ammonium nitrate, sulfuric acid, potassium sulfate, and sodium sulfate. They may be used alone or in combination with one another.

To perform oxidation, an adequate amount of the water-soluble oxidizing agent is added to an aqueous suspension of graphite flaky particles. The oxidation treatment makes the surface of graphite particles more hydrophilic. The oxidizing agent may be used under any conditions which ware not specifically limited. Adequate conditions (such as kind, amount, temperature, and pH) can be determined for effective oxidation so that the treatment leads to enhanced hydrophilicity. There are several preferred ways of performing the above-mentioned oxidation treatment. They are given below.

(1) Oxidation with potassium permanganate starts with the preparation of a suspension from 100 parts by weight of graphite flaky particles and 1,000-10,000 parts by weight of deionized water. To this suspension is added potassium permanganate in an amount of $1.0 \times 10^{-4}$ to $20 \times 10^{-4}$ g, preferably $4 \times 10^{-4}$ to $10 \times 10^{-4}$ g, per unit surface area (m$^2$) of graphite flaky particles. The suspension is allowed to stand at 5°–60° C. for 1–48 hours, preferably 3–24 hours. (One may surmise that potassium permanganate does not work any longer as an oxidizing agent once the graphite surface is oxidized, from the fact that the filtrate of the suspension containing excess potassium permanganate assumes a reddish color which indicates the capability of potassium permanganate to perform oxidation.)

(2) Oxidation with hydrogen peroxide starts with the dilution of hydrogen peroxide (1–20 parts by weight for 100 parts by weight of graphite flaky particles) with deionized water. To this dilute hydrogen peroxide is added a proper amount of graphite flaky particles to give a 1–10 wt % suspension. The suspension is adjusted to pH 1–7, preferably pH 3–6, with a acid substance, and is kept stirred for 12–96 hours. (Hydrogen peroxide is a stronger oxidizing agent than potassium permanganate; but it functions as a moderate oxidizing agent for graphite flaky particles suspended in an acid solution, although it undergoes vigorous exothermic reaction when added to an alkaline suspension.)

(3) Oxidation with an organic acid such as formic acid and acetic as a water-soluble oxidizing agent starts with the preparation of a suspension from 100 parts by weight of graphite flaky particles and 1,000–10,000 party by weight of deionized water. To this suspension are added 1.5–30 parts by weight, preferably 3–15 parts by weight of formic acid and 0.5–20 parts by weight, preferably 1–10 parts by weight, of hydrogen peroxide. The suspension is stirred for 10–100 hours, preferably 10–50 hours, at 5°–60° C.

(4) Oxidation with sulfuric acid as a water-soluble oxidizing agent starts with the preparation of a suspension from 100 parts by weight of graphite flaky particles and 1,000–10,000 parts by weight of deionized water. To this suspension is added 1–20 parts by weight of sulfuric acid. The suspension is kept at 60° C. to boiling point, preferably 90° C. to boiling point, for 1–24 hours.

(5) Oxidation with nitric acid as a water-soluble oxidizing agent starts with the preparation of a suspension from 100 parts by weight of graphite flaky particles and 1,000–10,000 party by weight of deionized water. To this suspension is added 1–20 parts by weight, preferably 5–15 parts by weight of nitric acid. The suspension is stirred at 20°–100° C. for 3–72 hours, preferably 12–48 hours. This procedure may be applied to nitrate such as potassium nitrate.

(6) Oxidation can be achieved more effectively by the use of two or more water-soluble oxidizing agents. In this case, the procedure starts with the preparation of a suspension from 100 parts by weight of graphite flaky particles and 1,000–10,000 parts by weight of deionized water. To this suspension is added potassium permanganate in an amount of $4 \times 10^{-4}$ to $10 \times 10^{-4}$ g per unit surface area (m$^2$) of graphite flaky particles. The suspension is stirred for 3–18 hours. To this suspension is further added 3–18 parts by weight of formic acid and 1.0–10 parts by weight of hydrogen peroxide, followed by stirring at 10°–60° C. for 5–72 hours.

(7) The above-mentioned oxidation with a water-soluble oxidizing agent in a suspension may be preceded by oxidation in an oxygen-containing atmosphere.

The above-mentioned oxidation process makes the graphite flaky particles highly dispersible in water. Among many methods for evaluating water dispersibility, the most practicable is to observe what happens when a small amount of oxidized graphite flaky particles is vigorously mixed with deionized water in a test tube. Dispersible graphite flaky particles orient in the flow direction, exhibiting the "stream line" which is an indication of good dispersibility. When mixed with water, unoxidized graphite flaky particles float on the water or agglomerate in the water, but do not exhibit the stream line.

No elucidation has been made yet of the mechanism by which the surface of graphite flaky particles is oxidized. It is considered that hydrophobic groups (such as $-CH=$, $-CH_2-$, $-CH_3$, and $-C=O$) on the surface are changed by oxidation into hydrophilic groups (such as $-OH$, $-COOH$, $-COSO_3H$, and $-COONa$), which are responsible for the improved dispersibility. The mechanism proposed is to be understood as hypothesis, and the inventors do not wish to be restricted to it.

Table 4 shows the dispersibility of oxidized graphite flaky particles obtained after different oxidation treatments, in water.

TABLE 4

| Dispersibility of Oxidized Graphite Flaky Particles in Water | |
|---|---|
| Condition of Oxidative Treatment | Dispersibility in Water of Oxidized Graphite |
| Heat oxidation (400° C. × 30 min.) | X-Δ |
| Heat oxidation (400° C. × 30 min.) + KMnO$_4$ 1% soln. (1 hr.) | Δ |
| Heat oxidation (400° C. × 30 min.) + KMnO$_4$ 1% soln. (3 hr.) | Δ |
| Heat oxidation (400° C. × 30 min.) + KMnO$_4$ 1% soln. (6 hr.) | Δ |
| Heat oxidation (400° C. × 30 min.) + KMnO$_4$ 1% soln. (12 hr.) | O |
| Heat oxidation (400° C. × 30 min.) + KMnO$_4$ 1% soln. (24 hr.) | O |

X, X-Δ, Δ, O
low dispersibility ⟶ high dispersibility

It can be derived from Table 4 that a combination of two oxidation steps, i.e.,
heating the graphite flaky particle in an oxygen-containing atmosphere, and
oxidation in an aqueous solution with a water-soluble oxidizing agent
is preferred. One can further conclude that the time of oxidation in water preferably should be at least 3 h.

The present invention is embodied to another aspect in a flaky pigment which comprises oxidized graphite flaky particles according to claim 1 the surface of which is coated with a metal oxide, preferably titanium dioxide hydrate and/or titanium dioxide. Any metal oxide suitable for use in the production of interference pigments may be used, e.g., as disclosed in U.S. Pat. No. 3,087,828, U.S. Pat. No. 3,087,829, U.S. Pat. No. 3,553,001, U.S. Pat. No. 3,650,790, U.S. Pat. No. 3,874,890, U.S. Pat. No. 3,926,659, U.S. Pat. No. 4,086,100, U.S. Pat. No. 4,456,486, U.S. Pat. No. 4,435,220, U.S. Pat. No. 4,565,581, U.S. Pat. No. 4,494,993, U.S. Pat. No. 4,509,988, U.S. Pat. No. 4,537,636, U.S. Pat. No. 4,545,821, U.S. Pat. No. 4,603,047, U.S. Pat. No. 4,867,793, U.S. Pat. No. 4,780,140 and U.S. Pat. No. 4,828,623.

This pigment according to the present invention is produced by any of the following processes (8) or (9).

(8) A process which involves suspending oxidized graphite particles in water, and adding to the suspension an aqueous solution of a titanium salt and an aqueous solution of a basic substance simultaneously, thereby depositing titanium dioxide hydrate uniformly and densely on the surface of the graphite flaky particles.

(9) A process which involves calcining at 450°-950° C. the graphite flaky pigment obtained by process (8).

The above-mentioned titanium salt includes, for example, titanium oxysulfate, titanic sulfate, titanous sulfate, and titanium tribromide.

The above-mentioned aqueous solution of basic substance includes, for example, an aqueous solution of sodium hydroxide, an aqueous solution of potassium hydroxide, and an aqueous solution of ammonium.

Any known process may be used to coat the surface or oxidized graphite flaky particles with titanium dioxide hydrate or titanium dioxide. For uniform, dense coating, it is desirable to add an aqueous solution of a titanium salt and a aqueous solution of a basic substance simultaneously to an aqueous suspension of oxidized graphite flaky particles, so as to deposit titanium dioxide hydrate on the surface of graphite flaky particles.

To carry out the above-mentioned process, the titanium salt may be hydrolyzed in the following manner. First, an aqueous suspension containing oxidized graphite flaky particles in an amount of 1-20 wt %, preferably 3-10 wt %, is adjusted to pH 0.5-5 with an acid substance such as hydrochloric acid, while stirring at 50°-100° C., preferably 70°-80° C. Second, an aqueous solution of a titanium salt is added to be aqueous suspension, using a metering pump, together with an aqueous solution of a basic substance which keeps the pH of the aqueous suspension constant. The titanium salt aqueous solution preferably has a concentration of 0.01-5.0 mol/liter. Also, the titanium salt aqueous solution preferably is added dropwise at a rate of $0.01 \times 10^{-5}$ to $30 \times 10^{-5}$ mol/liter per minute per m$^2$ of the surface area of oxidized graphite flaky particles. The aqueous solution of a basic substance preferably has a concentration of 0.025-10 mol/liter.

As the titanium salt aqueous solution is added dropwise in the manner mentioned above, the surface of oxidized graphite flaky particles is coated with titanium dioxide hydrate which produces an interference color of gold, red, purple, blue, or green. When a desired interference color is obtained, it is necessary to discontinue the addition of the titanium salt aqueous solution and basic substance aqueous solution. Then, to the suspension is added an aqueous solution of a basic substance so that the pH value conforms to the standard of industrial waste water. Finally, the suspension is filtered to separate solids, and the solids are washed with deionized water to remove water-soluble salts formed by neutralization. Washing, which is followed by drying, is desirable to improve the physical properties (such as water resistance and light resistance) of the finished pigment.

It is desirable that the graphite flaky pigment obtained as mentioned above be calcined at 450°-950° C. for 0.15-10 hours in an atmosphere (air or inert gas) which prevents the thermal decomposition of graphite. This calcination makes the titanium dioxide coating denser, permitting it to produce a superior, light-resistant interference color.

As mentioned above, the present invention provides a titanium dioxide-coated graphite flaky pigment which produces a good interference color owing to the uniform, dense titanium dioxide coating.

The present invention is embodied to another aspect in a flaky pigment which comprises oxidized graphite flaky particles the surface of which is coated with rutile titanium dioxide hydrate and/or rutile titanium dioxide.

The present invention is embodied in a further aspect by a flaky pigment which comprises oxidized graphite flaky particles and rutile titanium dioxide hydrate and/or rutile titanium dioxide together with silicon dioxide covering the surface of the particles.

According to the present invention, these flaky pigments are preferably produced by any one of the following processes (10) to (13).

(10) A process which involves suspending oxidized graphite flaky particles in water, adding to the suspension an aqueous solution of a titanium salt and a metal salt selected from tin salts, zinc salts, lithium salts, and antimony salts and an aqueous solution of a basic substance all at once, thereby depositing a mixture of titanium dioxide hydrate and metal oxide hydrate resulting from said metal salt on the surface of the graphite flaky particles, adding an aqueous solution of a titanium salt an aqueous solution of a basic substance all at once, thereby depositing titanium dioxide hydrate, and filtering the resulting solid substance, and washing, drying, and firing the solid substance.

(11) A process which consists of suspending oxidized graphite flaky particles in water, adding to the suspension an aqueous solution of a metal salt selected from tin salts, zinc salts, lithium salts, and antimony salts and an aqueous solution of a basic substance all at once, thereby depositing a metal oxide hydrate resulting from said metal salt on the surface of the graphite flaky particles, adding an aqueous solution of a titanium salt and an aqueous solution of a basic substance all at once, thereby depositing titanium dioxide hydrate, and filtering the resulting solid substance, and washing, drying, and firing the solid substance.

(12) A process according to process (10) mentioned above, in which the oxidized graphite flaky particles are those which are coated with silicon dioxide.

(13) A process according to process (11) mentioned above, in which the oxidized graphite flaky particles are those which are coated with silicon dioxide.

In the above-mentioned process (8), (9), (10) or (11), the oxidized graphite flaky particles may be previously coated with a metal oxide and/or metal oxide hydrate, said metal oxide including zirconium oxide, cobalt oxide, manganese oxide, chromium oxide, and cerium oxide.

The titanium salt used in the above-mentioned processes (10)-(13) includes, for example, titanium tetrachloride, titanium sulfate, titanium trichloride, titanous sulfate, titanic sulfate, and titanium tribromide.

The aqueous solution of a basic substance used in the above-mentioned processes (10)-(13) include, for example, aqueous solutions of sodium hydroxide, potassium hydroxide, and ammonium hydroxide.

According to the above mentioned processes (12) and (13), the oxidized graphite flaky particles are coated with silicon dioxide. This coating process should preferably be carried out by suspending the oxidized graphite flaky particles in water and adding to the suspension an aqueous solution of alkali silicate and an acid aqueous solution all at once. This coating process permits the uniform coating of silicon dioxide on the surface of oxidized graphite flaky particles in a simple manner. To be more specific, the aqueous suspension of oxidized graphite flaky particles preferably has a concentration of 3-15 wt %. After heating to 40°-90° C., the aqueous suspension should be adjusted to pH 1.8-3.0 with a acid aqueous solution or to pH 8-10 with an alkaline aqueous solution. To the suspension are added simultaneously an aqueous solution or alkali silicate through a metering pump and an acid aqueous solution through a metering pump, while keeping the desired pH. In this way, it is possible to deposit silicon dioxide on the surface of oxidized graphite flaky particles.

The above-mentioned alkali silicate is selected from sodium metasilicate, sodium orthosilicate, sodium disilicate, sodium tetrasilicate, potassium silicate, and sodium silicate. It is used in the form of aqueous solution having a concentration of 0.2-5 wt % in terms of silicon dioxide. The aqueous solution of alkali silicate should preferably be added dropwise at a rate of from $0.1 \times 10^{-5}$ to $10 \times 10^{-5}$ mol/liter (in terms of silicon dioxide) per minute per unit area (m$^2$) of graphite flaky particles.

The above-mentioned acid aqueous solution includes, for example, aqueous solutions of hydrochloric acid, sulfuric acid, and nitric acid.

According to the above-mentioned processes (10)-(13), the salt of a metal selected from tin, zinc, lithium, and antimony is used to make titanium dioxide that or rutile structure. Examples of the metal salt include stannous chloride, stannic chloride, stannous sulfate, zinc chloride, zinc sulfate, zinc nitrate, lithium chloride, lithium sulfate, lithium nitrate, antimony oxychloride, and antimony trichloride. Tin salts are preferable because of their high performance and good handleability. These metal salts may be used alone or in combination with one another. They are preferably used in an amount of 0.01-50 wt % (as metal oxide) for titanium dioxide used for coating.

According to the above-mentioned processes (10)-(13), oxidized graphite flaky particles or silicon dioxide-coated graphite flaky particles are coated with a metal oxide hydrate and titanium dioxide hydrate, said metal oxide including tin oxide, zinc oxide, lithium oxide, and antimony oxide. This coating step may be carried out by any known method.

The amount of titanium dioxide hydrate used for the coating of oxidized graphite flaky particles or silicon dioxide-coated graphite flaky particles should be properly controlled so that the resulting titanium dioxide-coated graphite flaky pigment produces a desired color. This is accomplished by adding an aqueous solution of a metal salt and an aqueous solution of a basic substance all at once to the aqueous suspension of oxidized graphite flaky particles or silicon dioxide-coated graphite flaky particles so that a hydrate of a metal oxide (selected from tin oxide, zinc oxide, lithium oxide, and antimony oxide) is deposited on the surface of oxidized graphite flaky particles or silicon dioxide-coated graphite flaky particles.

To be more specific, this process is carried out as follows: First, oxidized graphite flaky particles or silicon dioxidecoated graphite flaky particles are dispersed in water to make an aqueous suspension having a concentration of 1-20 wt %, preferably 3-10 wt %. After heating to 50°-100° C., preferably 70°-80° C., with stirring, the aqueous solution is adjusted to pH 0.5-5.0 with an acid substance such as hydrochloric acid. To the aqueous suspension are added simultaneously an aqueous solution of a metal salt through a metering pump and a aqueous solution of a basic substance to keep a constant pH level. The aqueous solution of a metal salt preferably has a concentration of from 0.01 to 5.0 mol/liter. The aqueous solution of a metal salt should preferably be added dropwise at a rate of from $0.01 \times 10^{-5}$ to $30 \times 10^{-5}$ mol/liter per minute per unit area (m$^2$) of oxidized graphite flaky particles or silicon dioxide-coated graphite flaky particles. The aqueous solution of a basic substance should preferably have a concentration of 0.025-10 mol/liter.

In the above-mentioned process oxidized graphite flaky particles or silicon dioxide-coated graphite flaky particles are coated with a hydrate of a metal oxide (selected from tin oxide, zinc oxide, lithium oxide, and antimony oxide) and a hydrate of titanium dioxide. The resulting coating produces various interference colors (gold, red, blue, and green) in proportion to the amount of the aqueous solution of the metal salt added. When a desired interference color is obtained, it is necessary to discontinue the addition of the aqueous solution of a metal salt and the aqueous solution of a basic substance. Then, the suspension is neutralized with an alkaline aqueous solution so that its pH value conforms to the standard for industrial waste water. Finally, the suspension is filtered to separate the pigment formed. The pigment is washed with deionized water to remove water-soluble salts formed by neutralization. Washing is desirable to improve the water resistance, light resistance, and weather resistance of the finished pigment. After washing, the pigment is dried at 100°-200° C. for 2-20 hours and then fired at 450°-1000° C. for 0.15-10 hours in air or an inert gas that suppresses the decomposition of graphite, Firing improves the weather resistance and light resistance of the pigment.

As mentioned above, the present invention provides flaky pigments with superior properties and especially with a good light resistance, weather resistance and/or chromaticity, in particular in comparison with conventional titanium dioxidecoated graphite flaky pigments.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding Japanese applications 91-177834, filed Apr. 18, 1991, and 91-221316, filed May 24, 1991, are hereby incorporated by reference.

EXAMPLES

The first group of experiments comprising comparative example 1, examples 1-16 and application examples 1-4 refers to pigments which comprise oxidized graphite flaky particles the surface of which is coated with titanium dioxide hydrate and/or titanium dioxide.

Comparative Example 1

A graphite flaky pigment was prepared as follows according to the conventional technology involving no oxidation. In 1000 ml of deionized water was suspended with stirring 10 g of graphite flaky particles having a particle diameter ranging from 1 to 100 $\mu$m, with an average particle diameter being 36 $\mu$m ("PB-85" made by Nishimura Kokuen Co., Ltd.). The suspension was heated to 75° C. and gently bubbled with air at this temperature. To the suspension was added dropwise with stirring a titanium trichloride solution containing 24.6 g of 35 wt % hydrochloric acid and 49.3 g of 20.3 wt % titanium trichloride in 2000 ml of deionized water, at a rate of 3.75 ml/min using a metering pump, until the suspension became acidified to pH 2.1. The dropwise addition of the titanium trichloride solution was continued at the same rate until the total amount of the solution reached 1837 ml. During this step, a 9.76 wt % aqueous solution of sodium hydroxide was also added dropwise to keep the suspension at pH 2.1. Then, the suspension was adjusted to pH 5 with a 9.76 wt % aqueous solution of sodium hydroxide, and filtered to separate the solid product. The solid product was washed with deionized water and then dried at 200° C. for 15 hours Thus there was obtained a red pigment with poor color development. Microscopic examination revealed that there are a larger number of particles producing no color and individual particles produce varied colors. In addition, it was found by observation under a scanning electron microscope that the coating of graphite flaky particles with titanium dioxide is uneven.

Example 1

Oxidation was performed on 10 g of graphite flaky particles ("PB.85" made by Nishimura Kokuen Co., Ltd.) having a particle an diameter ranging from 1 to 100 $\mu$m, with an average particle diameter being 36 $\mu$m, by heating in air at 350° C. for 30 minutes. The oxidized graphite flaky particles were suspended in 100 ml of deionized water. The resulting suspension underwent the same procedure as in Comparative Example for coating with titanium dioxide. Thus there was obtained a titanium dioxide-coated graphite flaky pigment which exhibits a red interference color. Microscopic examination revealed that the pigment contains only a small number of particles producing no color. In addition, it was found by observation under a scanning electron microscope that the coating of graphite flaky particles with titanium dioxide is almost uniform. The measurements of color tone indicate that the pigment in this example is superior in color development to that in Comparative Example 1.

Example 2

Oxidation was performed on 10 g of graphite flaky particles ("PB-85" made by Nishimura Kokuen Co., Ltd.) having a particle diameter ranging from 1 to 100 $\mu$m, with an average particle diameter being 36 $\mu$m, by heating in air at 450° C. for 30 minutes. The oxidized graphite flaky particles were suspended in 1000 ml of deionized water. (The oxidized graphite flaky particles more readily dispersed in water than those in Example 1). The resulting suspension underwent the same procedure as in Comparative Example 1 for coating with titanium dioxide. Thus there was obtained a titanium dioxidecoated graphite flaky pigment which exhibits a red interference color. Microscopic examination revealed that the pigment contains only a small number of particles producing no color. In addition, it was found by observation under a scanning electron microscope that the coating of graphite flaky particles with titanium dioxide is considerably uniform. The measurements of color tone indicate that the pigment in this example is superior in color development to that in Comparative Example 1.

Example 3

In 240 ml of deionized water was suspended with stirring 15 g of graphite flaky particles ("PB-85" made by Nishimura Kokuen Co., Ltd.) having a particle diameter ranging from 1 to 100 $\mu$m, with an average particle diameter being 36 $\mu$m. For oxidation of the graphite flaky particles, 0.15 g of potassium permanganate was added to the suspension, followed by stirring at normal temperature for 18 hours. The suspension was filtered to separate the oxidized graphite flaky particles, which were subsequently washed with deionized water and dried at 110° C. for 15 hours. To 10 g of the oxidized graphite flaky particles was added 1000 ml of deionized water with stirring to make a suspension. The oxidized graphite flaky particles readily dispersed in water. The resulting suspension underwent the same procedure as in Comparative Example 1 for coating with titanium dioxide. Thus there was obtained a titanium dioxide-coated graphite flaky pigment which exhibits a red interference color. Microscopic examination revealed that the pigment consists of flaky particles exhibiting a uniform color. In addition, it was found by observation under a scanning electron microscope that the coating of graphite flaky particles with titanium dioxide is uniform. The measurements of color tone indicate that the pigment in this example is by far superior in color development to that in Comparative Example 1.

Example 4

Preliminary oxidation was performed on 15 g of graphite flaky particles ("PB-85" made by Nishimura Kokuen Co., Ltd.) having a particle diameter ranging from 1 to 100 $\mu$m, with an average particle diameter being 36 $\mu$m, by heating in air at 450° C. for 30 minutes. The oxidized graphite flaky particles were suspended in 240 ml of deionized water. For further oxidation of the graphite flaky particles, 0.15 g of potassium permanganate was added to the suspension, followed by stirring at normal temperature for 18 hours. The suspension was filtered to separate the oxidized graphite flaky particles, which were subsequently washed with deionized water and dried at 110° C. for 15 hours. To 10 g of the oxidized graphite flaky particles was added 1000 ml of deionized water with stirring to make a suspension. The oxidized graphite flaky particles readily dispersed in water. The resulting suspension underwent the same procedure as in Comparative Example 1 for coating with titanium dioxide. Thus there was obtained a titanium dioxide-coated graphite flaky pigment which exhibits a red interference color. Microscopic examination revealed that the pigment consists of particles exhibiting a uniform color. In addition, it was found by observation under a scanning electron microscope that the coating of graphite flaky particles with titanium dioxide is uniform. The measurements of color tone indicate that the pigment in this example is by far superior in color development to that in Comparative Example 1.

Example 5

Preliminary oxidation was performed on 15 g of graphite flaky particles ("PB-85" made by Nishimura Kokuen Co., Ltd.) having a particle diameter ranging from 1 to 100 μm, with an average particle diameter being 36 μm, by heating in air at 450° C. for 30 minutes. The oxidized graphite flaky particles were suspended in 240 ml of deionized water. For further oxidation of the graphite flaky particles, 0.15 g of potassium permanganate and 0.12 g of 62 wt % nitric acid were added to the suspension, followed by stirring at normal temperature for 18 hours. The suspension was filtered to separate the oxidized graphite flaky particles, which were subsequently washed with deionized water and dried at 110° C. for 15 hours. To 10 g of the oxidized graphite flaky particles was added 1000 ml of deionized water with stirring to make a suspension. The oxidized graphite flaky particles readily dispersed in water. The resulting suspension underwent the same procedure as in Comparative Example 1 for coating with titanium dioxide. Thus there was obtained a titanium dioxide-coated graphite flaky pigment which exhibits a red interference color. Microscopic examination revealed that the pigment consists of particles exhibiting a uniform color. In addition, it was found by observation under a scanning electron microscope that the coating of graphite flaky particles with titanium dioxide is uniform. The measurements of color tone indicate that the pigment in this example is by far superior in color development to that in Comparative Example 1.

Example 6

Preliminary oxidation was performed on 15 g of graphite flaky particles ("PB-85" made by Nishimura Kokuen Co., Ltd.) having a particle diameter ranging from 1 to 100 μm, with an average particle diameter being 36 μm, by heating in air at 450° C. for 30 minutes. The oxidized graphite flaky particles were suspended in 240 ml of deionized water. For further oxidation of the graphite flaky particles, 5.1 g of 87 wt % formic acid and 4.35 g of 34.5 wt % hydrogen peroxide were added to the suspension, followed by stirring at normal temperature for 18 hours. The suspension was filtered to separate the oxidized graphite flaky particles, which were subsequently washed with deionized water and dried at 110° C. for 15 hours. To 10 g of the oxidized graphite flaky particles was added 1000 ml of deionized water with stirring to make a suspension. The oxidized graphite flaky particles readily dispersed in water. The resulting suspension underwent the same procedure as in Comparative Example 1 for coating with titanium dioxide. Thus there was obtained a titanium dioxide-coated graphite flaky pigment which exhibits a reddish-purple interference color. Microscopic examination revealed that the pigment consists of particles exhibiting a uniform color. In addition, it was found by observation under a scanning electron microscope that the coating of graphite flaky particles with titanium dioxide is uniform. The measurements of color tone indicate that the pigment in this example is by far superior in color development to that in Comparative Example 1.

Examples 7 to 11

Each graphite flaky pigment obtained in Examples 2 to 6 was calcined in air at 520° C. for 30 minutes. The calcined pigment exhibited a better interference color.

Examples 12 to 16

Each graphite flaky pigment obtained in Examples 2 to 6 was calcined in nitrogen at 600° C. for 30 minutes. The calcined pigment exhibited a better interference color. The results obtained in Comparative Example and Examples are shown in Tables 1 and 2.

TABLE 1

| | Oxidation of graphite flake particles | Color of titanium dioxide-coated graphite flake particles, observed by microscope | Coating of titanium dioxide, observed by scanning electron microscope | Titanium dioxide coating (%) | Hunter color index (45°/0°), L value | Hunter color index (45°/0°), a value | Hunter color index (45°/0°), b value | Saturation $\sqrt{a^2 + b^2}$ | Evaluation of color | Diameter of graphite flake particles (μm) |
|---|---|---|---|---|---|---|---|---|---|---|
| Comparative Example | Not oxidized | Considerably uneven | Uneven | 32.2 | 18.4 | 2.3 | 0.9 | 2.5 | poor | 1–100 |
| Example 1 | 350° C. × 30 min | Uneven | Slightly uneven | 32.2 | 17.3 | 2.9 | −1.2 | 3.1 | fair | 1–100 |
| Example 2 | 450° C. × 30 min | Slightly uneven | Slightly uneven | 32.2 | 17.4 | 2.5 | −3.5 | 4.3 | fair | 1–100 |
| Example 3 | 1% KMnO$_4$ | Slightly uneven | Slightly uneven | 32.2 | 17.4 | 3.9 | −0.6 | 3.9 | fair | 1–100 |
| Example 4 | 450° C. × 30 min 1% KMnO$_4$ | Considerably uniform | Almost uniform | 32.2 | 17.7 | 4.2 | −0.9 | 4.3 | good | 1–100 |
| Example 5 | 450° C. × 30 min 1% KMnO$_4$, 0.5% HNO$_3$ | Considerably uniform | Very slightly uneven | 32.2 | 16.9 | 4.2 | 2.4 | 4.8 | good | 1–100 |
| Example 6 | 450° C. × 30 min 10% H$_2$O$_2$, 29.3% HCOOH | Uniform | Uniform | 32.2 | 16.6 | 4.7 | −5.0 | 6.9 | good | 1–100 |

TABLE 2

| | Pigment calcined | Atmosphere for calcination | Temperature for calcination (°C.) | Time for calcination (min) | Hunter color index (45°/0°), L value | Hunter color index (45°/0°), a value | Hunter color index (45°/0°), b value | Saturation $\sqrt{a^2 + b^2}$ | Evaluation of color |
|---|---|---|---|---|---|---|---|---|---|
| Example 7 | Pigment obtained in Example 2 | Air | 520 | 30 | 17.3 | 2.2 | −4.3 | 4.8 | fair |
| Example 8 | Pigment obtained in Example 3 | Air | 520 | 30 | 17.7 | 4.2 | −3.2 | 5.2 | fair |
| Example 9 | Pigment obtained in Example 4 | Air | 520 | 30 | 17.7 | 4.4 | −2.9 | 5.3 | good |
| Example 10 | Pigment obtained in Example 5 | Air | 520 | 30 | 17.3 | 4.1 | −3.8 | 5.6 | good |
| Example 11 | Pigment obtained in Example 6 | Air | 520 | 30 | 17.0 | 4.1 | −6.4 | 7.6 | good |
| Example 12 | Pigment obtained in Example 2 | Nitrogen | 600 | 30 | 18.3 | 1.3 | −4.6 | 4.8 | fair |
| Example 13 | Pigment obtained in Example 3 | Nitrogen | 600 | 30 | 17.9 | 4.1 | −4.9 | 6.4 | good |
| Example 14 | Pigment obtained in Example 4 | Nitrogen | 600 | 30 | 17.5 | 4.3 | −4.8 | 6.4 | good |
| Example 15 | Pigment obtained in Example 5 | Nitrogen | 600 | 30 | 17.6 | 3.9 | −5.3 | 6.6 | good |
| Example 16 | Pigment obtained in Example 6 | Nitrogen | 600 | 30 | 17.6 | 3.3 | −7.5 | 8.2 | good |

Notes to Tables 1 and 2
For more information about L-value, a-value, and b-value, refer to JIS Handbook; "Iro no kagaku" (Science of color): "Kagaku no hanashi shiriizu 9" (Chemical Stories 9), issued by Baifukan, pp. 39–46; and "Shikizai kogaku handobukku" (Color material handbook), issued by Asakura Shoten, pp. 190–211.

Application Examples

The graphite flaky pigment of the present invention can be used for automotive top coating, plastic coloring, printing ink, electric appliance finish coating, lacquer, and cosmetics. For automotive top costing, it may be used alone or in combination with an organic pigment, carbon black, metal powder (such as aluminum powder), or mica-based pearl pigment, in an amount of 0.1-50 wt % of the top coating resin. This is illustrated in Application Example 1 below.

Application Example 1

| | |
|---|---|
| Acrylic-melamine resin | 100 wt % |
| "Acrydec 47-712" | 70 wt % |
| "Superbeckamine G821-60" | 30 wt % |
| Pigment obtained in Example 16 | 20 wt % |
| Ethyl acetate | 50 wt % |
| Toluene | 30 wt % |
| n-butanol | 10 wt % |
| Solvesso #150 | 40 wt % |

The acrylic-melamine resin was diluted with the thinner to achieve a desired viscosity (12–15 seconds with Ford cup #4) for spray coating.

Application Example 2

The graphite flaky pigment was used for plastics coloring (by dry blending) according to the following formulation. The resulting blend was used for injection molding.

| | |
|---|---|
| Polyethylene resin (pellets) | 100 pbw |
| Pigment obtained in Example 16 | 1 pbw |
| Zince stearate | 0.2 pbw |
| Liquid paraffin | 0.1 pbw |

Application Example 3

The graphite flaky pigment was used for gravure printing ink according to the following formulation. The resulting ink was diluted with NC-102 solvent (made by Toyo Ink) to achieve a desired viscosity (20 sec with Zahn cup No. 3).

| | |
|---|---|
| CCT medium (nitrocellulose resin, Toyo Ink) | 40 pbw |
| Pigment obtained in Example 16 | 8 pbw |

Application Example 4

The graphite flaky pigment (having a particle diameter smaller than 4.5 μm) was used for cake-type eyeshadow according to the following recipe.

| | |
|---|---|
| Graphite flake pigment | 40 pbw |
| Talc | 24 pbw |
| Mica | 10 pbw |
| Zinc stearate | 5.0 pbw |
| Zinc laurate | 3.0 pbw |
| Coloring pigment | 10 pbw |
| Hexadecyl myristate | 5.5 pbw |
| Lanolin fatty acid isopropyl | 1.5 pbw |
| Antiseptic | q.s. |

The second group of experiments comprising Comparative Example 2, examples 17–20 and application examples 5–8 refers to pigment according to claim 3 and 4 which comprise oxidized graphite flaky particles the surface of which is coated with rutile titanium dioxide hydrate and/or rutile titanium dioxide (claim 3) resp. which comprise oxidized graphite flaky particles and rutile titanium dioxide hydrate and/or rutile titanium dioxide together with silicon dioxide covering the surface of the particles.

Comparative Example 2

In 240 ml of deionized water was suspended with stirring 15 g of graphite flaky particles having a particle diameter ranging from 1 to 100 μm, with an average particle diameter being 36 μm ("PB-85" made by Nishimura Kokuen Co., Ltd.). For oxidation, the suspension was stirred together with 0.15 g of potassium permanganate at normal temperature for 18 hours. The suspension was filtered off to separate the oxidized graphite flaky particles, which were subsequently washed with deionized water and dried at 110° C. for 15 hours. 10 g of the oxidized graphite flaky particles was suspended with stirring in 1000 ml of deionized water. The suspension was heated to 75° C. and gently bubbled with air at this temperature. To the suspension was added dropwise with stirring a solution containing 24.6 g of 35 wt % hydrochloric acid and 49.3 g of 20.3 wt % titanium trichloride in 2000 ml of deionized water, at a rate of 3.75 ml/min using a metering pump, until the suspension became acidified to pH 2.1. The dropwise addition of the solution was continued at the same rate while keeping the pH value at 2.1 by adding dropwise a 9.76 wt % aqueous solution of sodium hydroxide.

In this way the solution of titanium trichloride was added dropwise in a total amount of 1837 ml. Then, the suspension was adjusted to pH 5 with a 9.76 wt % aqueous solution of sodium hydroxide, and filtered to separate the solid product. The solid product was washed with deionized water and then dried at 200° C. for 15 hours. Thus there was obtained a graphite flaky pigment coated with titanium dioxide hydrate.

This pigment was washed with deionized water, collected by filtration, dried at 200° C. for 15 hours, and fired at 520° C. for 30 minutes. Thus there was obtained a titanium dioxidecoated graphite flaky pigment which produces a good red interference color. Microscopic examination revealed that this titanium dioxide has the anatase crystal structure. This pigment was tested for weather resistance using a carbon arc weatherometer (made by Suga Shikenki Co., Ltd.).

Example 17

A titanium dioxide-coated graphite flaky pigment was prepared. The process started with oxidation of graphite flaky particles ("PB-85" made by Nishimura Kokuen Co., Ltd.) having a particle diameter ranging from 1 to 100 µm, with an average particle diameter being 36 µm, by heating in air at 450° C. for 30 minutes. 20 g of the oxidized graphite flaky particles was suspended in 500 ml of deionized water. The resulting suspension underwent oxidation by stirring together with 0.2 g of potassium permanganate at normal temperature for 15 hours. The suspension was filtered to separate the oxidized graphite flaky particles, which were subsequently washed with deionized water ro remove residual potassium permanganate. 20 g of the oxidized graphite flaky particles was dispersed in 250 g of deionized water. After heating to 75° C., the suspension was adjusted to pH 1.8 with a 10 wt % aqueous solution of hydrochloric acid. To the suspension was added dropwise a mixture of 13.2 ml of aqueous solution containing 53 g/liter of stannic chloride pentahydrate and 1.86 ml of aqueous solution containing 407 g/liter of titanium tetrachloride, at a rate of 0.2 ml/min. At the same time, a 5 wt % aqueous solution of sodium hydroxide was added dropwise to keep the suspension at pH 1.8. In this way titanium dioxide hydrate and tin dioxide hydrate were deposited on the surface of graphite flaky particles.

The process was continued by adding to the suspension 160 ml of a mixed solution composed of 80 ml of aqueous solution containing 407 g/liter of titanium tetrachloride and 80 ml of 10 wt % aqueous solution of hydrochloric acid, at a rate of 0.2 ml/min. At the same time, a 5 wt % aqueous solution of sodium hydroxide was added to keep the suspension at pH 1.8. In this way titanium dioxide hydrate was deposited. After the addition of the mixed solution, a 5 wt % aqueous solution of sodium hydroxide was added to adjust the suspension from pH 1.8 to pH 6.0. The resulting solid product was collected by filtration, washed with deionized water, and dried at 130° C. for 15 hours. There was obtained a graphite flaky pigment coated with titanium dioxide hydrate which produces a good gold interference color. This pigment was fired in air at 520° C. for 30 minutes to give a titanium dioxide-coated graphite flaky pigment which produces a good gold interference color.

On examination by X-ray diffractometry, it was found that the titanium dioxide in this pigment has the rutile crystal structure. Moreover, the results of weathering test by Suga's carbon arc sunshine weatherometer indicate that this pigment is by far superior in weather resistance to the graphite flaky pigment coated with anatase titanium dioxide which was obtained in Comparative Example 2.

Example 18

A titanium dioxide-coated graphite flaky pigment was prepared. The process started with oxidation of graphite flaky particles ("PB-85" made by Nishimura Kokuen Co., Ltd.) having a particle diameter ranging from 1 to 100 µm, with an average particle diameter being 36 µm, by heating in air at 450° C. for 30 minutes. 20 g of the oxidized graphite flaky particles was suspended in 500 ml of deionized water. The resulting suspension underwent oxidation by stirring together with 0.2 g of potassium permanganate at normal temperature for 15 hours. The suspension was filtered to separate the oxidized graphite flaky particles, which were subsequently washed with deionized water ro remove residual potassium permanganate. 20 g of the oxidized graphite flaky particles was dispersed in 250 g of deionized water. After heating to 75° C., the suspension was adjusted to pH 1.8 with a 10 wt % aqueous solution of hydrochloric acid. To the suspension was added dropwise 8.8 ml of aqueous solution containing 53 g/liter of stannic chloride at a rate of 0.2 ml/min. At the same time, a 5 wt % aqueous solution of sodium hydroxide was added dropwise to keep the suspension at pH 1.8. In this way stannic dioxide was deposited on the surface of graphite flaky particles.

The process was continued by adding to the suspension 160 ml of a mixed solution composed of 80 ml of aqueous solution containing 407 g/liter of titanium tetrachloride and 80 ml of 10 wt % aqueous solution of hydrochloric acid, at a rate of 0.2 ml/min. At the same time, a 5 wt % aqueous solution of sodium hydroxide was added to keep the suspension at pH 1.8.

In this way titanium dioxide hydrate was deposited. After the addition of the mixed solution, a 5 wt % aqueous solution of sodium hydroxide was added to adjust the suspension from pH 1.8 to pH 6.0. The resulting solid product was collected by filtration, washed with deionized water, and dried at 130° C. for 15 hours. There was obtained a pigment which produces a good violet interference color. This pigment was fired in air at 520° C. for 30 minutes to give a titanium dioxide-coated graphite flaky pigment which produces a good violet interference color.

On examination by X-ray diffractometry, it was found that the titanium dioxide in this pigment has the rutile crystal structure. Moreover, the results of weathering test by Suga's carbon arc sunshine weatherometer indicate that this pigment is considerably superior in weather resistance to the graphite flaky pigment coated with anatase titanium dioxide which was obtained in Comparative Example 2.

Example 19

A titanium dioxide-coated graphite flaky pigment was prepared. The process started with oxidation of graphite flaky particles ("PB-85" made by Nishimura Kokuen Co., Ltd.) having a particle diameter ranging from 1 to 100 μm, with an average particle diameter being 36 μm, by heating in air at 450° C. for 30 minutes. 20 g of the oxidized graphite flaky particles was suspended in 500 ml of deionized water. The resulting suspension underwent oxidation by stirring together with 0.2 g of potassium permanganate at normal temperature for 15 hours. The suspension was filtered to separate the oxidized graphite flaky particles, which were subsequently washed with deionized water ro remove residual potassium permanganate.

20 g of the oxidized graphite flaky particles was dispersed in 250 g of deionized water. After heating to 60° C., the suspension was adjusted to pH 9.5 with a 5 wt % aqueous solution of sodium hydroxide. To the suspension was added dropwise 24 g of aqueous solution of sodium silicate (equivalent to 1.7 wt % of silicon dioxide) at a rate of 0.2 ml/min using a metering pump. At the same time, a 3.5 wt % aqueous solution of hydrochlorid acid was added dropwise using a metering pump to keep the suspension at pH 9.5. After the addition of the sodium silicate aqueous solution, a 3.5 wt % aqueous solution of hydrochloric acid was added to adjust the suspension to pH-6.0. The resulting silicon dioxide-coated graphite flaky particles were collected by filtration.

The silicon dioxide-coated graphite flaky particles were washed with deionized water to remove residual water-soluble salts formed by neutralization. After drying at 105° C. for 15 hours, the silicon dioxide-coated graphite flaky particles were further coated with rutile titanium dioxide in the same manner as in Example 17.

On examination by X-ray diffractometry, it was found that the resulting pigment is coated with rutile titanium dioxide. Moreover, the results of weathering test by Suga's carbon arc sunshine weatherometer indicate that this pigment is by far superior in weather resistance to the graphite flaky pigment coated with anatase titanium dioxide which was obtained in Comparative Example 2.

Example 20

A titanium dioxide-coated graphite flaky pigment was prepared. The process started with oxidation of graphite flaky particles ("PB-85" made by Nishimura Kokuen Co., Ltd.) having a particle diameter ranging from 1 to 100 μm, with an average particle diameter being 36 μm, by heating in air at 450° C. for 30 minutes. 20 g of the oxidized graphite flaky particles was suspended in 500 ml of deionized water. The resulting suspension underwent oxidation by stirring together with 0.2 g of potassium permanganate at normal temperature for 15 hours. The suspension was filtered to separate the oxidized graphite flaky particles, which were subsequently washed with deionized water ro remove residual potassium permanganate. 20 g of the oxidized graphite flaky particles was dispersed in 250 g of deionized water. After heating to 60° C., the suspension was adjusted to pH 9.5 with a 5 wt % aqueous solution of sodium hydroxide. To the suspension was added dropwise 24 g of aqueous solution of sodium silicate (equivalent to 1.7 wt % of silicon dioxide) at a rate of 0.2 ml/min using a metering pump. At the same time, a 3.5 wt % aqueous solution of hydrochlorid acid was added dropwise using a metering pump to keep the suspension at pH 9.5. After the addition of the sodium silicate aqueous solution, a 3.5 wt % aqueous solution of hydrochloric acid was added to adjust the suspension to pH 6.0. The resulting silicon dioxide-coated graphite flaky particles were collected by filtration.

The silicon dioxide-coated graphite flaky particles were washed with deionized water to remove residual water-soluble salts formed by neutralization. After drying at 105° C. for 15 hours, the silicon dioxide-coated graphite flaky particles were further coated with rutile titanium dioxide in the same manner as in Example 18.

On examination by X-ray diffractometry, it was found that the resulting pigment is coated with rutile titanium dioxide. Moreover, the results of weathering test by Suga's carbon arc sunshine weatherometer indicate that this pigment is by far superior in weather resistance to the graphite flaky pigment coated with anatase titanium dioxide which was obtained in Comparative Example 2.

Weathering test

The pigments obtained in Comparative Example 2 and in Examples 17-20 were tested for weather resistance by subjecting a test piece (prepared in the following manner) to weathering in Suga's carbon arc sunshine weatherometer. Weather resistance was rated according to the color difference ($\Delta E$) which was observed after the weathering test.

Preparation of test piece

A bonderized mild steel sheet was undercoated with "Superlac F47 Black" (arylic resin made by Nippon Paint Co., Ltd.) in a thickness of 35–40 μm, followed by baking at 150° C. for 30 minutes. The undercoating was polished with sand paper (#600), washed, and dried at 110° C. The undercoating was coated with an intermediate coating, 18–20 μm thick (of the following formulation) and a clear top coating, 35–40 μm thick (of the following formulation), followed by baking at 140° C. for 20 minutes.

| Intermediate coating | |
|---|---|
| Pigment pertaining to the invention | 20 pbw |
| Acrydic 47-712* | 70 pbw |
| Superbeckamine G821-60* | 30 pbw |
| Ethyl acetate | 50 pbw |
| Toluene | 30 pbw |
| n-butanol | 10 pbw |
| Solvesso #150 | 40 pbw |
| Clear topcoating | |
| Acrydic 44-179* | 14 pbw |
| Superbeckamine L117-60* | 6 pbw |
| Toluene | 4 pbw |
| MIBK | 4 pbw |
| Butyl cellosolve | 3 pbw |

*Products of Dainippon Ink & Chemicals, Inc.

The specimen underwent weathering test in Suga's carbon arc sunshine weatherometer, with 12-minute rainfall in each 60-minute cycle, at a black panel temperature of 63° C. The results are shown in Table 3.

TABLE 3

| | Crystal structure of titanium dioxide | Duration of weathering test and color difference ΔE*) after weathering test | | |
|---|---|---|---|---|
| | | 60 hrs | 120 hrs | 240 hrs |
| Comparative Example 2 | Anatase | 7.4 | 9.0 | 12.6 |
| Example 17 | Rutile | 0.2 | 0.4 | 0.1 |
| Example 18 | Rutile | 0.4 | 0.4 | 0.5 |
| Example 19 | Rutile | 0.2 | 0.3 | 0.2 |
| Example 20 | Rutile | 0.2 | 0.1 | 0.2 |

Color difference ΔE* was measured with CR-200 made by Minolta Co., Ltd. (For more detail about color difference DE*, refer to JIS Handbook.)

Applications of pigment pertaining to the invention

As mentioned above, the present invention provides a graphite flaky pigment coated with rutile titanium dioxide. It will find use a pigment for automotive top coating paint, plastics coloring, printing ink, house-hold appliance paint, architectural paint, Japanese lacquer, and cosmetics. It is particularly suitable for outdoor paints, plastics, and inks because of its superior weather resistance and light resistance. When used for automotive paints, it is added in an amount of 0.1-50 wt % to the intermediate coating, alone or in combination with carbon black, organic pigments, aluminum powder or other metal powered, or mica-based pearlescent pigment.

Application Example 5 (for automotive paint)

| Acrylic/melamine resin (for intermediate coating) | |
|---|---|
| Acrydic 47-712* | 70 pbw |
| Superbeckamine G-821-60* | 30 pbw |
| Graphite pigment obtained in Example 17 | 20 pbw |
| Thinner for acrylic/melamine resin | |
| Ethyl acetate | 50 pbw |
| Toluene | 30 pbw |
| n-butanol | 10 pbw |
| Solvesso #150 | 40 pbw |

*Products of Dainippon Ink & Chemcials, Inc.

The acrylic/melamine resin was diluted with the thinner until a proper viscosity (12-15 seconds by Ford cup #4) was reached. The resulting paint was applied by spraying to form the intermediate coating.

Application Example 6 (for plastics coloring)

| Polyethylene resin (pellets) | 100 pbw |
|---|---|
| Pigment obtained in Example 17 | 1 pbw |
| Zinc stearate | 0.2 pbw |
| Liquid paraffin | 0.1 pbw |

After dry blending, the resulting compound was used for injection molding.

Application Example 7 (for gravure printing ink)

| CCST medium (nitrocellulose resin)* | 40 pbw |
|---|---|
| Pigment obtained in Example 17 | 8 pbw |

*Product of Toyo Ink Mfg. Co., Ltd.

The CCST medium containing the pigment was diluted with NC-102 solvent (made by Toyo Ink) until a desired viscosity (20 sec with Zahn cup No. 3) was reached.

Application Example 8 (for cosmetics)

A recipe for cake-type eye-shadow is given below.

| Pigment of the invention* | 40 pbw |
|---|---|
| Talc | 24 pbw |
| Mica | 10 pbw |
| Zinc stearate | 5.0 pbw |
| Zinc laurate | 3.0 pbw |
| Coloring pigment | 10 pbw |
| Hexadecyl myristate | 5.5 pbw |
| Lanolin fatty acid isopropyl | 2.5 pbw |
| Antiseptic | q.s. |

*with a particle diameter smaller than 4.5 μm

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An oxidized graphite flaky particle obtained by a process comprising:
   (a) oxidizing graphite flaky particles in an oxygen-containing atmosphere at 200°-500° C.,
   (b) suspending graphite flaky particles in water and oxidizing said particles with a water-soluble oxidizing agent, or
   (c) a combination of (a) and (b).

2. A graphite flaky particle according to claim 1, prepared by a process comprising oxidizing graphite flaky particles in an oxygen-containing atmosphere, suspending said oxidized particles in water and additionally oxidizing said particles with a water-soluble oxidizing agent.

3. A flaky pigment comprising an oxidized graphite flaky particle according to claim 1, the surface of which is coated with a metal oxide hydrate and/or metal oxide.

4. A flaky pigment according to claim 3, wherein the metal oxide hydrate and/or metal oxide is titanium oxide hydrate or titanium dioxide.

5. A flaky pigment comprising an oxidized graphite flaky particle according to claim 4, the surface of which is coated with rutile titanium dioxide hydrate and/or rutile titanium dioxide.

6. A flaky pigment which comprises an oxidized graphite flaky particle according to claim 1, coated with rutile titanium dioxide hydrate and/or rutile titanium dioxide together with silicon dioxide.

7. A process for the production of a flaky pigment comprising suspending oxidized graphite flaky particles in water and adding to the suspension an aqueous solution of a metal salt and an aqueous solution of a basic substance simultaneously, thereby depositing metal oxide hydrate uniformly and densely on the surface of the graphite flake particles.

8. A process for the production of a flaky pigment, comprising
   (a) oxidizing graphite flaky particles in an oxygen-containing atmosphere, (b) suspending graphite flaky particles in water and oxidizing said particles with a water-soluble oxidizing agent, or (c) a combination of (a) and (b), (d) suspending said particles in water and adding to the suspension an aqueous solution of a metal salt and a basic substance, thereby depositing metal oxide hydrate on the surface of the particles.

9. A process according to claim 8, comprising oxidizing graphite flake particles in an oxygen-containing atmosphere, suspending said oxidized particles in water and additionally oxidizing said particles with a water-soluble oxidizing agent, and suspending said particles in water and adding to the suspension an aqueous solution of a metal salt and a basic substance, thereby depositing metal oxide hydrate on the surface of the particles.

10. A process according to claim 7 which further comprises calcining the flaky pigment.

11. A process according to claim 8 which further comprises calcining the flaky pigment.

12. A process according to claim 9 which further comprises calcining the flaky pigment.

13. A process for producing a flaky pigment according to claim 5 which comprises suspending oxidized graphite flaky particles in water, adding to the suspension an aqueous solution of a titanium salt and a metal salt selected from the group consisting of tin salts, zinc salts, lithium salts and antimony salts, and an aqueous solution of a basic substance, thereby depositing a mixture of titanium dioxide hydrate and metal oxide hydrate resulting from said metal salt on the surface of the graphite flaky particles, adding an aqueous solution of a titanium salt and an aqueous solution of a basic substance, thereby depositing titanium dioxide hydrate, and filtering the resulting solid substance, and washing, drying, and firing the solid substance.

14. A process for producing a flaky pigment according to claim 5 which comprises suspending oxidized graphite flaky particles in water, adding to the suspension an aqueous solution of a metal salt selected from the group consisting of tin salts, zinc salts, lithium salts and antimony salts, and an aqueous solution of a basic substance, thereby depositing a metal oxide hydrate resulting from said metal salt on the surface of the graphite flaky particles, adding an aqueous solution of a titanium salt and an aqueous solution of a basic substance, thereby depositing titanium dioxide hydrate, and filtering the resulting solid substance, and washing, drying, and firing the solid substance.

* * * * *